US010076636B2

(12) United States Patent
Murray et al.

(10) Patent No.: US 10,076,636 B2
(45) Date of Patent: Sep. 18, 2018

(54) COMPACT CATHETER ASSEMBLY WITH ADJUSTABLE CATHETER TUBE

(71) Applicant: Hollister Incorporated, Libertyville, IL (US)

(72) Inventors: Michael G. Murray, Ballina (IE); Adam J. Foley, Ballina (IE); Eugene Canavan, Bray (IE); James Jackson, Dublin (IE)

(73) Assignee: HOLLISTER INCORPORATED, Libertyville, IL (US)

( * ) Notice: Subject to any disclaimer, the term of this patent is extended or adjusted under 35 U.S.C. 154(b) by 349 days.

(21) Appl. No.: 14/775,493

(22) PCT Filed: Mar. 14, 2013

(86) PCT No.: PCT/US2013/031735
§ 371 (c)(1),
(2) Date: Sep. 11, 2015

(87) PCT Pub. No.: WO2014/142930
PCT Pub. Date: Sep. 18, 2014

(65) Prior Publication Data
US 2016/0067445 A1 Mar. 10, 2016

(51) Int. Cl.
*A61M 27/00* (2006.01)
*A61M 25/00* (2006.01)
*A61M 25/01* (2006.01)

(52) U.S. Cl.
CPC .... *A61M 25/0043* (2013.01); *A61M 25/0017* (2013.01); *A61M 25/002* (2013.01); *A61M 25/0111* (2013.01)

(58) Field of Classification Search
CPC .......... A61M 25/0043; A61M 25/0017; A61M 25/002; A61M 25/0111
See application file for complete search history.

(56) References Cited

U.S. PATENT DOCUMENTS

| 5,653,700 A | * | 8/1997 | Byrne | A61M 25/01 604/328 |
|---|---|---|---|---|
| 2003/0004496 A1 | | 1/2003 | Tanghoj | |
| 2004/0158231 A1 | | 8/2004 | Tanghoj et al. | |

FOREIGN PATENT DOCUMENTS

| WO | WO 2005/014055 A2 | 2/2005 |
|---|---|---|
| WO | WO 2008/009590 A1 | 1/2008 |
| WO | WO 2011/019359 A1 | 2/2011 |

OTHER PUBLICATIONS

International Search Report, for International Application No. PCT/US2013/031735, dated Dec. 20, 2013.
Written Opinion of the International Searching Authority for International Application No. PCT/US2013/031735, dated Dec. 20, 2013.

* cited by examiner

*Primary Examiner* — Philip R Wiest
(74) *Attorney, Agent, or Firm* — Cook Alex Ltd.

(57) ABSTRACT

A compact catheter assembly is disclosed. The catheter assembly includes a receiver and a catheter sub-assembly. The catheter sub-assembly includes a catheter tube a fluid drain that are adapted for relative pivotal movement about a fluid junction.

22 Claims, 9 Drawing Sheets

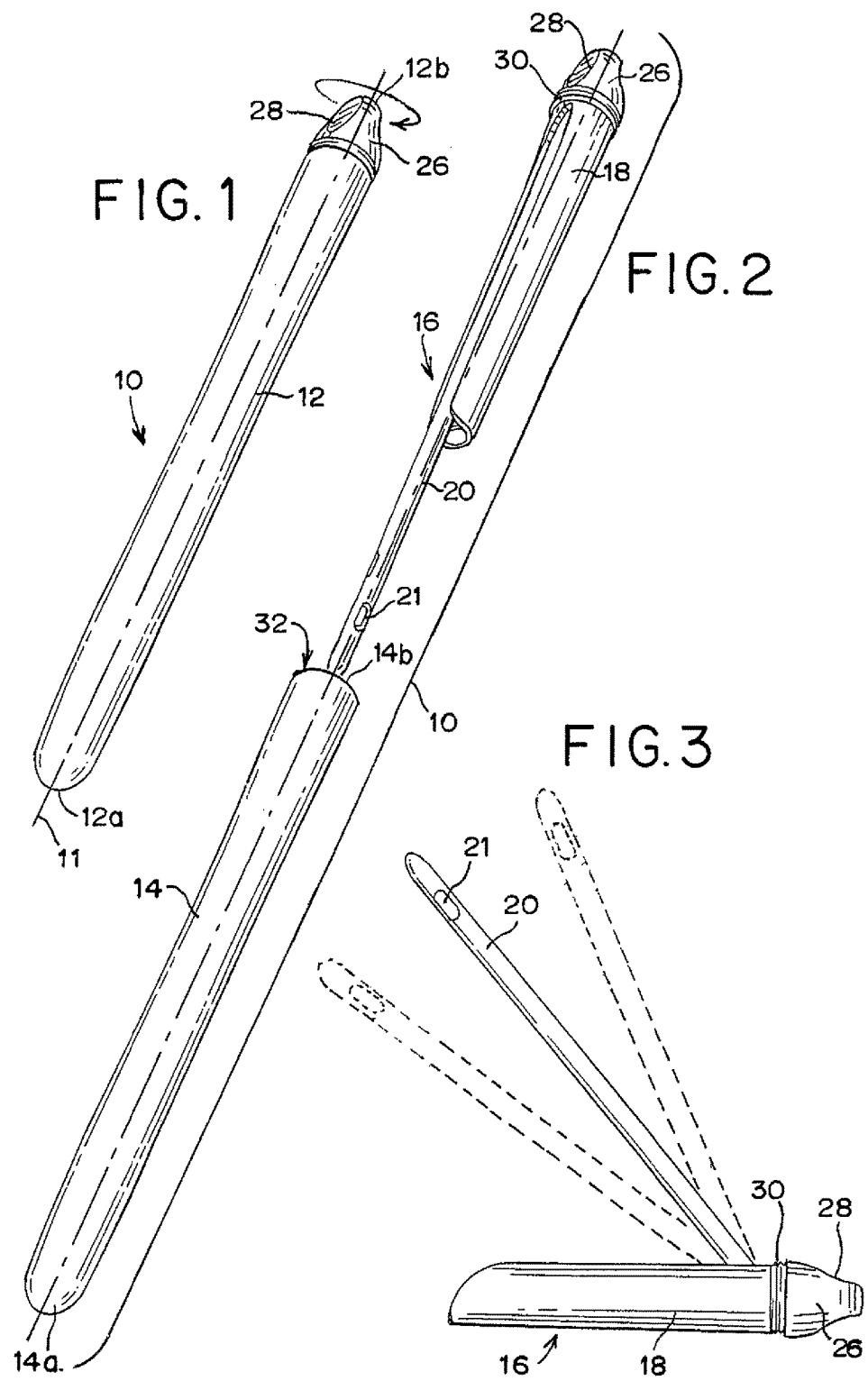

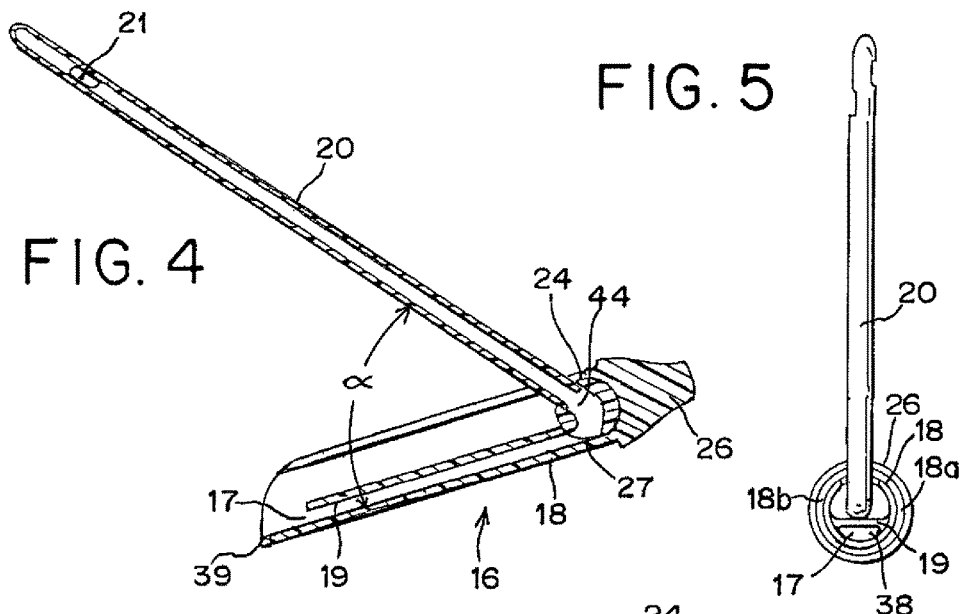
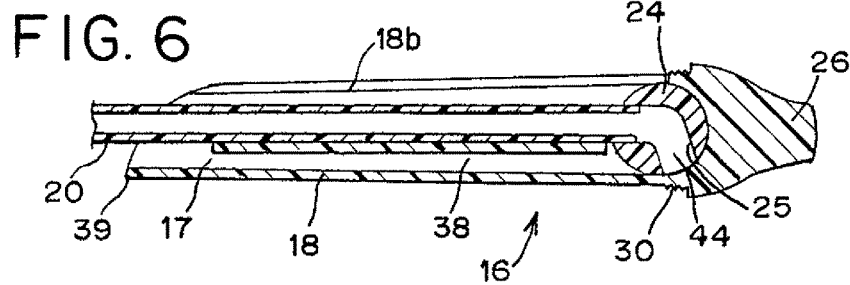
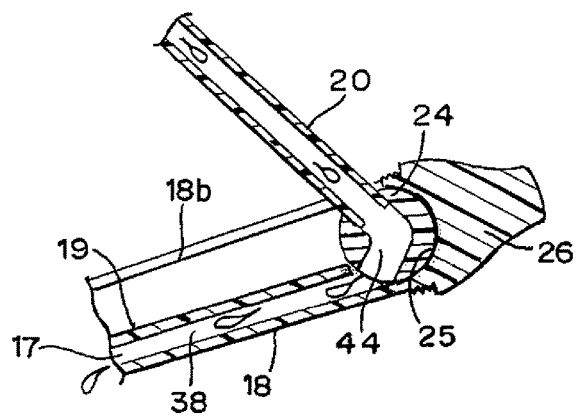

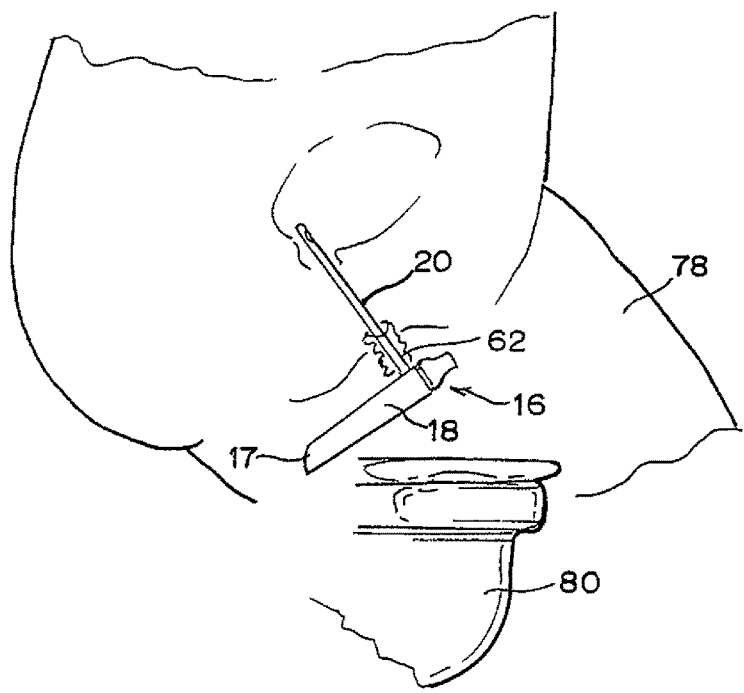
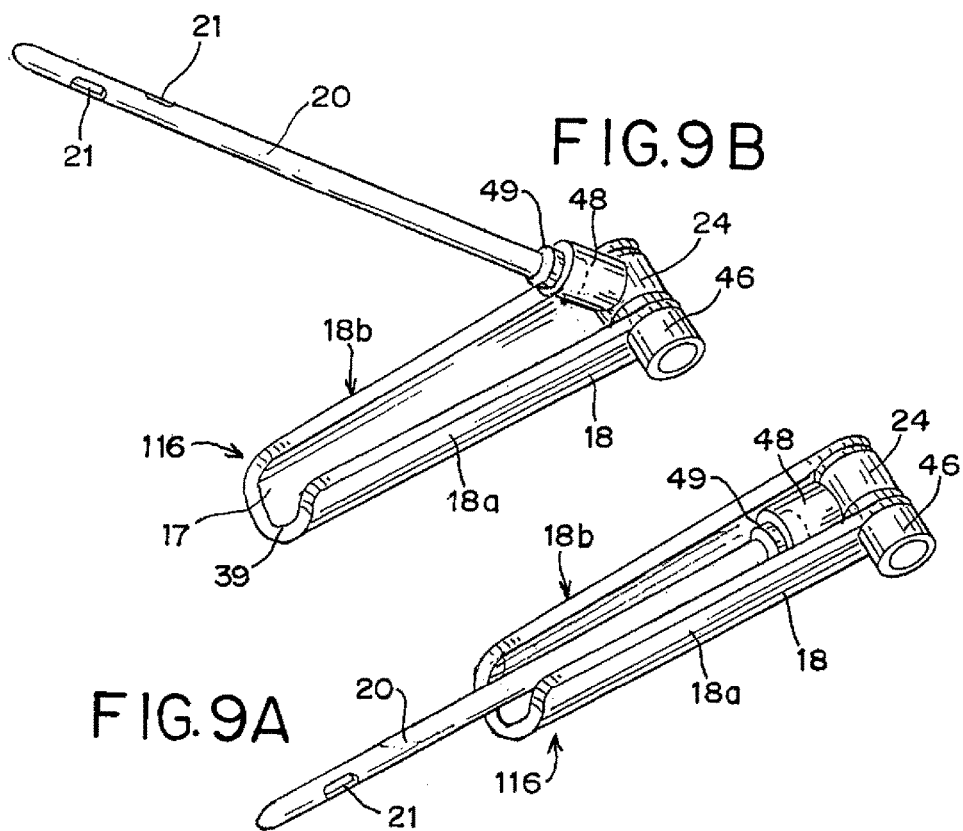

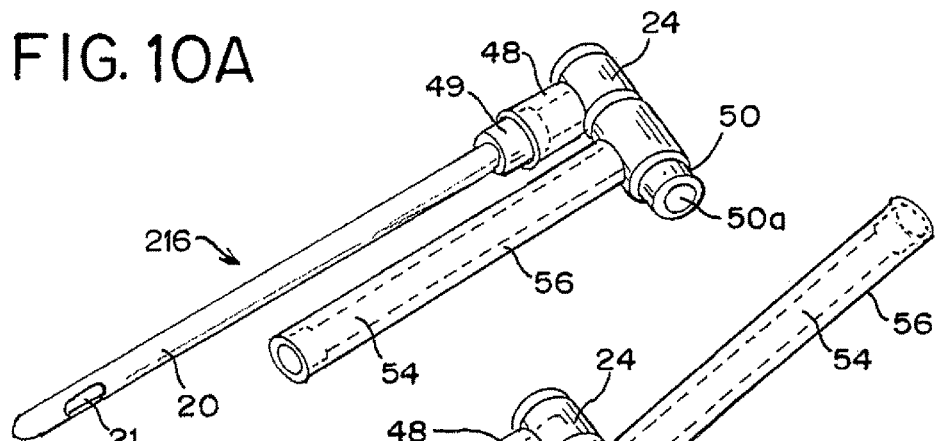
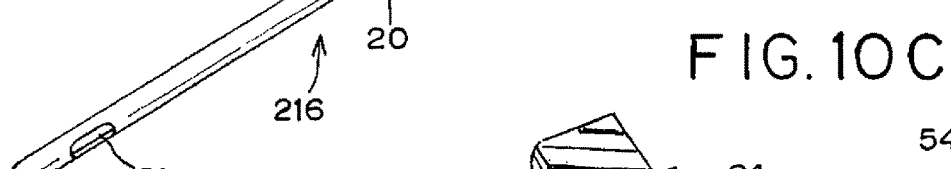
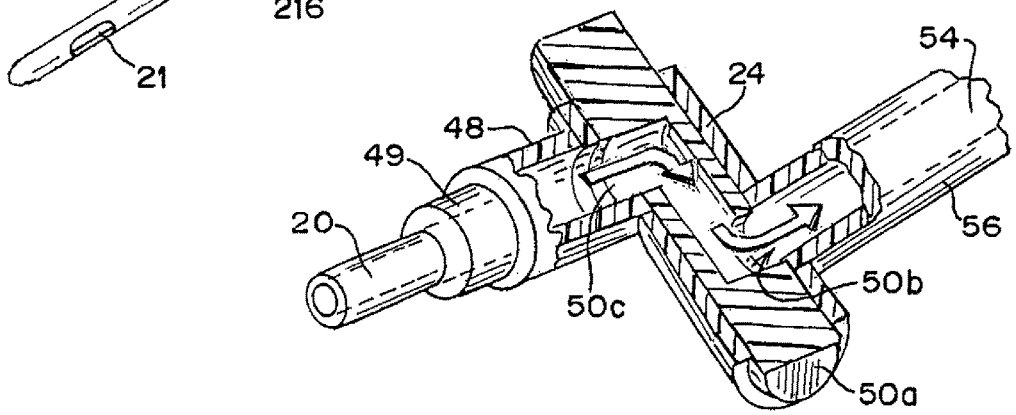
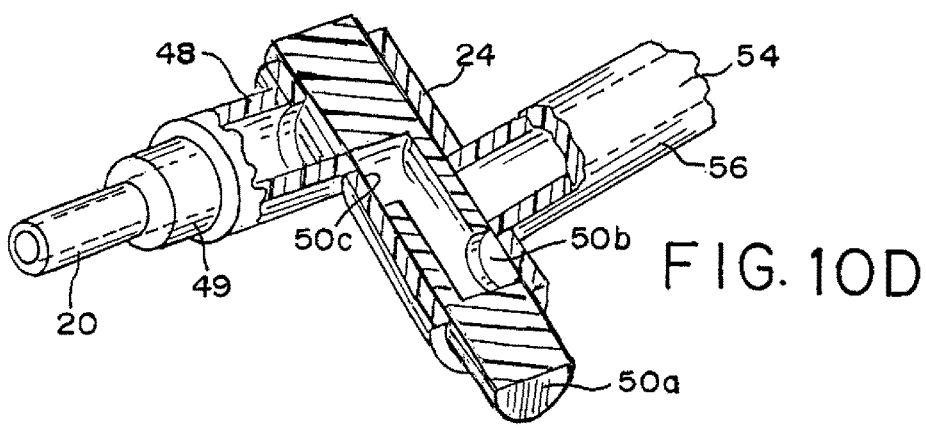

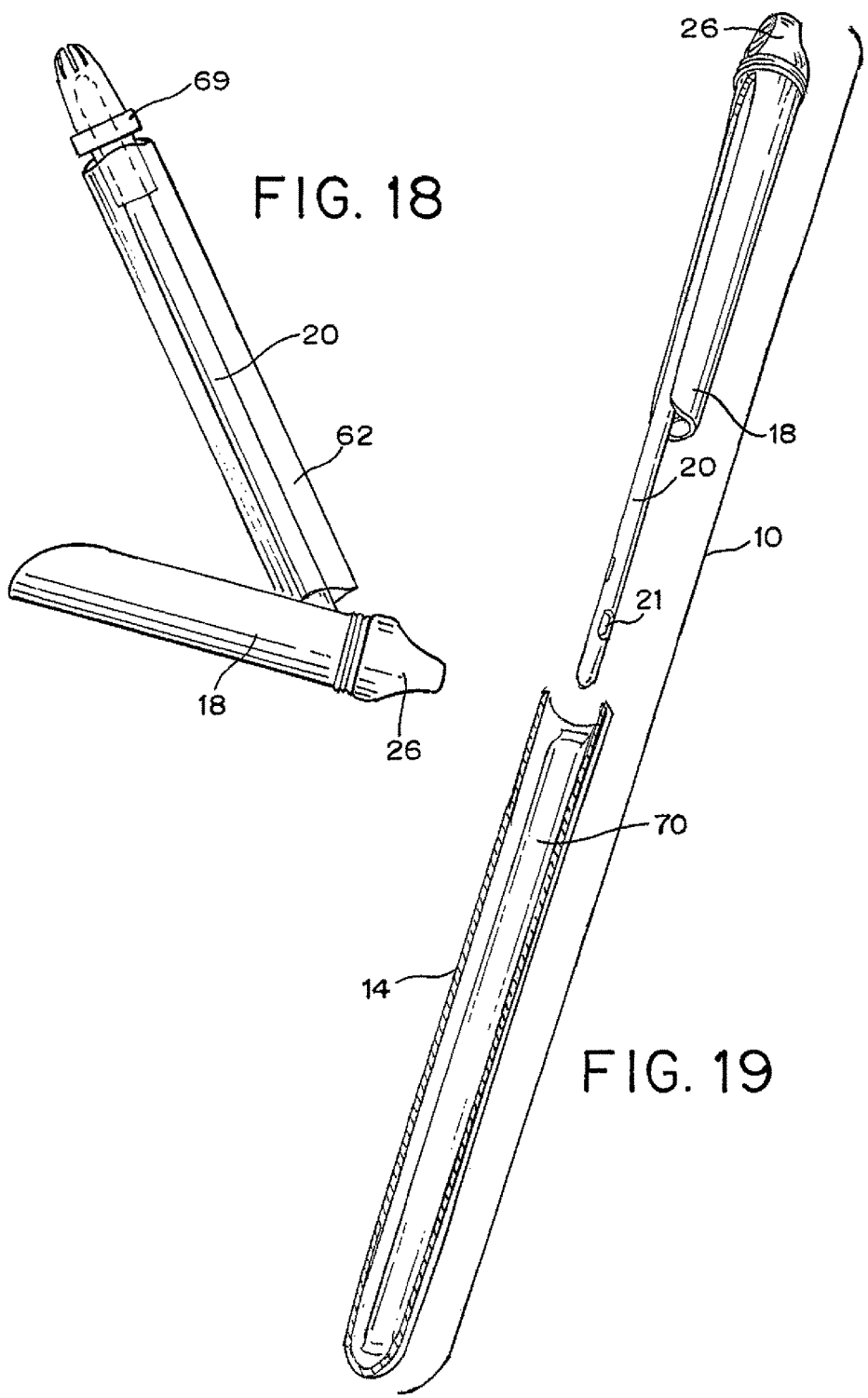

COMPACT CATHETER ASSEMBLY WITH ADJUSTABLE CATHETER TUBE

The present application is the U.S. National Stage of PCT International Patent Application No. PCT/US2013/031735, filed Mar. 14, 2013, which is incorporated herein by reference.

FIELD OF THE DISCLOSURE

The present disclosure is directed to catheters for use in the medical field. More particularly, the present disclosure is directed to catheters for use in the treatment of urinary incontinence. Even more particularly, the present disclosure is directed to compact, portable urinary catheters that are easily manipulated and adjusted by the user.

BACKGROUND

Catheters are used to treat many different types of medical conditions and typically include an elongated catheter tube that is inserted into and through a passageway or lumen of the body. Urinary catheters and, in particular, intermittent urinary catheters are commonly used by individuals who suffer from certain abnormalities of the urinary system, such as urinary incontinence. With the advent of intermittent urinary catheters, individuals with problems associated with the urinary system can conveniently self-catheterize to drain the individual's bladder. Individuals who suffer from urinary incontinence will self-catheterize several times a day.

Self-catheterization involves removing the catheter assembly from its package and inserting and advancing the catheter tube through the user's urethra. In many cases, users of intermittent urinary catheters have limited or diminished dexterity that is often the result of spinal cord injuries. Users of intermittent catheters are often required to self-catheterize outside the privacy of the home, such as in public restrooms. Thus, for these and other reasons, it is desirable that the intermittent catheters are provided in discrete packaging that is easy to open, compact and portable, and wherein the catheter can be deployed and used in a way that alleviates concerns about inadvertent urine leakage or spillage and avoids pain or discomfort to the user.

BRIEF DESCRIPTION OF THE DRAWINGS

FIG. 1 is a perspective view of a catheter assembly of the present disclosure in its assembled state;

FIG. 2 is a is perspective view of the catheter assembly of FIG. 1 in its separated state;

FIG. 3 is a side view of a catheter sub-assembly with a catheter tube in a plurality of deployed orientations;

FIG. 4 is a cross-sectional side view the catheter sub-assembly of FIG. 3;

FIG. 5 is an end view of a catheter sub-assembly of FIG. 3 with the catheter tube in a deployed orientation;

FIG. 6 is a partial, cross-sectional side view of the catheter sub-assembly of FIG. 3 with a catheter tube in the non-deployed orientation;

FIG. 7 is a partial, cross-sectional side view of the catheter assembly of FIGS. 5-6 showing flow through the catheter assembly when the catheter tube is in the deployed orientation and flow communication has been established;

FIG. 8 shows the catheter sub-assembly of FIG. 3 with the catheter tube and drain in a relatively pivoted position during use;

FIG. 9A is a perspective view of another embodiment of a catheter sub-assembly of the present disclosure with the catheter tube in its initial position;

FIG. 9B is a perspective view of the catheter sub-assembly of FIG. 9A with the catheter tube in its deployed position;

FIG. 10A is a perspective view of yet another embodiment of a catheter sub-assembly of the present disclosure in its initial position;

FIG. 10B is a perspective view of the catheter sub-assembly of FIG. 10A in a deployed position;

FIG. 10C is a cross-sectional top view of the fluid junction and flow controller of the catheter sub-assembly of FIG. 10B in the open-flow position;

FIG. 10D is a cross-sectional top view of the fluid junction and flow controller of the catheter sub-assembly of FIG. 10B in the closed flow position;

FIG. 18 is a side view of the catheter sub-assembly of the present disclosure with a full-length sleeve over the catheter tube and an introducer tip on the catheter tube; and FIG. 19 is a perspective view of a catheter assembly of the present disclosure with the receiver in cross-section and a hydration element contained within the receiver.

SUMMARY

Figure 11A:
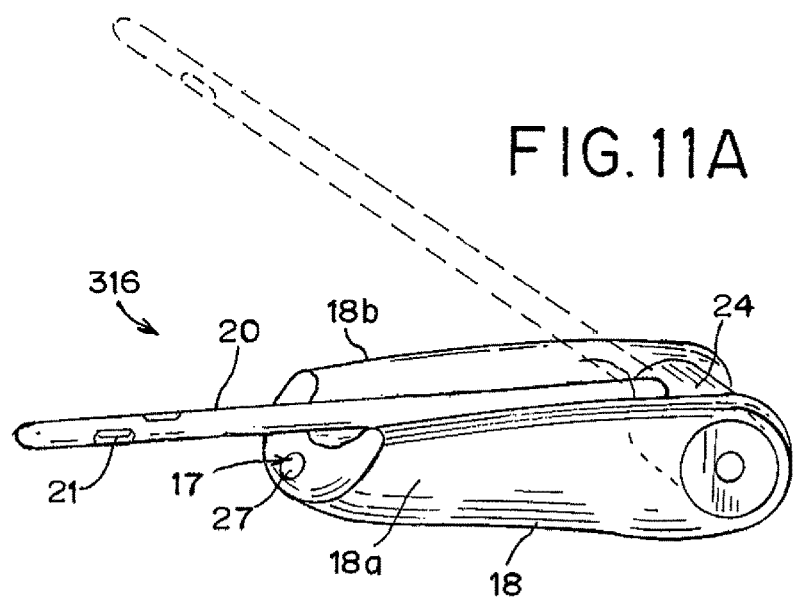
FIG. 11A is a is a perspective view of still another embodiment of a catheter sub-assembly of the present disclosure with the catheter tube in a plurality of positions.

In one aspect, the present disclosure is directed to a catheter assembly that includes a catheter sub-assembly and a receiver. The catheter sub-assembly includes a fluid drain, a fluid junction that has a flow path defined therein and a catheter tube. The catheter tube likewise defines a flow path and is carried by the fluid junction. The catheter tube and the fluid drain are relatively pivotally movable about the fluid junction. The receiver defined an elongated housing that includes an interior chamber for receiving the catheter sub-assembly.

In another aspect, the present disclosure is directed to a catheter sub-assembly that includes a fluid drain, a fluid junction that has a flow path defined therein, and a catheter tube that likewise defines a flow path. The flow path of the catheter tube communicates with and is carried by the fluid junction. The catheter tube and the fluid drain are relatively pivotally movable about the junction.

In a more specific aspect, the catheter assemblies and sub-assemblies disclosed herein may include a hydration element contained within the receiver for activating the hydrophilic surface of the catheter tube.

In a more specific aspect, the catheter assemblies and sub-assemblies may include a handle that defines the fluid drain. The drain may be an open drain or an internal lumen defined within the body of the handle.

In another more specific aspect, the catheter assemblies and sub-assemblies disclosed herein may include a fluid junction that is a rotary member. Even more specifically, the rotary member may be a spherical member or a spool.

In another more specific aspect, the catheter assemblies and sub-assemblies disclosed herein may include fluid junctions where the flow paths in such junctions are non-linear.

In a further more specific aspect, the catheter assemblies and sub-assemblies disclosed herein may include an actuator for effecting relative movement of the catheter tube and the drain.

In still another, more specific aspect, the catheter assemblies and catheter sub-assemblies disclosed herein may include a flow controller for controlling the flow of fluid through such assemblies. The flow controller may be a switch or a button that when activated by the user starts and/or stops flow.

In yet another more specific aspect, the catheter assemblies and sub-assemblies disclosed herein may include a partial or substantially full-length sleeve disposed over the catheter tube. The catheter tubes, whether sleeveless or with such partial or full-length sleeves may also include an introducer tip.

In another more specific aspect, the catheter assemblies and sub-assemblies disclosed herein, the receiver may be made of rigid material. The receiver and the entire housing of the catheter assembly may be opaque and include a smooth outer surface. Alternatively, the receiver and/or the housing may be made of a non-rigid, flexible material.

DESCRIPTION OF THE ILLUSTRATED EMBODIMENTS

The embodiments disclosed herein are for the purpose of providing a description of the present subject matter. The catheter assemblies, catheter sub-assemblies, methods of use and methods of manufacture disclosed herein may be embodied in various other forms and combinations not specifically described or illustrated in any figure. Therefore, specific embodiments are not to be interpreted as limiting, and the features disclosed and illustrated are not to be interpreted as limited to any one specific embodiment as described or illustrated.

FIGS. 1 and 2 illustrate a catheter assembly 10 in accordance with the present disclosure. As shown in FIG. 2, the catheter assembly 10 includes a receiver 14 and catheter sub-assembly 16 which, when assembled, define elongated housing 12 of FIG. 1. Elongated housing 12 includes a proximal end 12a and distal end 12b. The terms "distal" and "proximal" are used throughout this disclosure. When used in the context of the catheter tube that is inserted into the body of the user, the term "proximal" is used to refer to an end or portion of a catheter tube that is closer in proximity to the user's body and/or enters the user's body. The term "distal" is used to refer to an end or portion that is opposite the proximal end or portion and is typically further away from the user's body. For the sake of consistency, when the terms "distal" and "proximal" are used in the context of a housing or a member that receives or carries the catheter tube such as the receiver or handle (which are not intended for insertion into the body), a proximal end or a proximal portion thereof is that end or portion closer to the proximal end of the catheter tube when the catheter tube is housed or carried by such housing or member, while the distal end or portion is opposite to such proximal end or portion.

As shown in FIG. 2, receiver 14 includes closed proximal end 14a and an open distal end 14b. Receiver 14 includes an outer surface and an inner surface that defines an interior chamber 15. As shown in the FIGS. 1 and 2, receiver 14 is preferably generally cylindrical and has a generally circular profile about central longitudinal axis 11. In a preferred embodiment, as shown in FIGS. 1 and 2, receiver 14 flares slightly outwardly near open distal end 14b and tapers inwardly along at least portion of its length, terminating in a generally rounded closed end 14a. Receiver 14 preferably includes a smooth outer surface with no sharp corners of edges.

Receiver 14 preferably includes an engagement surface at or near the open distal end 14b. In an embodiment, engagement surface may be an internal or external threaded surface which engages a corresponding thread on catheter assembly 16, as shown in FIGS. 1-4 and described below. Preferably, receiver 14 and housing 12 are made of a rigid, lightweight polymeric material, such as Nylon, ABS, polyethylene and polycarbonate.

In one embodiment, catheter sub-assembly 16 includes a handle 18, catheter tube 20 and, as shown in FIG. 4, fluid junction 24. Catheter assembly 16 may also include a pre-attached cap 26. As best seen in FIG. 2, catheter sub-assembly is contained within receiver 14 prior to use and may be returned to receiver 14 after use for disposal as a closed, single unit. Thus, catheter sub-assembly is sized for easy insertion and withdrawal into and from receiver 14.

Catheter tube 20 is attached to and carried by handle 18 of catheter sub-assembly 16. As shown in FIGS. 2-7, catheter tube 20 and handle 18 are relatively moveable to each other. More specifically, catheter tube 20 and handle 18 are adapted for relative pivotal movement. Such relative movement of catheter tube 20 and handle 18 is effected by fluid junction 24 which is likewise carried by handle 18 and is described in greater detail below.

As indicated above, catheter sub-assembly 16 includes cap 26, which seals open receiver end 14b. As noted above, cap 26 includes an engagement surface 30 which cooperates with a corresponding engagement surface 32 at receiver distal end 14b. As shown in FIGS. 3-7, in one embodiment, cap 26 may be generally conically shaped. Cap 26 may further include depressions or recesses in its outer surface to provide finger grip regions 28.

Handle 18 is preferably made of a polymeric material, likewise rigid and lightweight, which provides a stiff support for catheter tube 20. During insertion and/or withdrawal of catheter tube 20, a stiffer handle 18 reduces the need for added stiffness to catheter tube 20 while allowing the user to advance and direct catheter tube 20 through the urinary canal. This, in turn, allows for a less stiff tube that provides more comfort to the user during advancement and withdrawal of catheter tube 20 from the urethra. Materials that are suitable for use in handle 18 include the materials described above in connection with the manufacture of receiver 14, such as Nylon, ABS, polyethylene and polycarbonate.

As further shown in FIG. 5, handle 18 may be generally cylindrical, providing lateral arcuate walls 18a and 18b that can be grasped by the user during use. Handle 18 may include a partially open (top) wall that defines a longitudinal gap 36 extending along the length of handle 18. Gap 36 is sized to allow for angular deployment of tube 20 therethrough. As shown in FIGS. 4-7, handle 18 includes a fluid drain 17 for directing fluid out of catheter sub-assembly 16. In one embodiment, handle 18 includes an interior lumen 38 that extends through the body of handle 18 and is separated by wall 19 from the compartment in which catheter tube 20 resides before deployment. Lumen 38 serves as drain 17 and provides a flow path for the urine drained from the user's bladder. Lumen 38 terminates at its proximal end in a spout portion 39.

In one embodiment, handle 18 may be integrally formed with cap 26 and engagement surface 30. Thus, in the embodiment of FIGS. 2-7, handle 18, cap 26 and engagement surface 30 (e.g., threaded portion) may be integrally molded by, for example, injection molding. Alternatively, handle 18 may be molded or made separately from cap 26 and such handle and cap may then be assembled together with catheter tube 20 to provide catheter sub-assembly 16. In one such embodiment, catheter tube 20 with fluid junction 24 may be attached to or inserted into handle 18, and cap 26 is then attached to the distal end of handle 18.

Catheter tube 20 is typically made of a flexible, biocompatible polymeric material. Suitable polymers include polyvinyl chloride, polyvinyl pyrrolidone (PVP), as well as other materials such as polyamide, polyanhydride, polyether, poly (ether imide), poly(ester imide), polyvinyl alcohol, polyvinyl chloride, polycarbonate, poly($\varepsilon$-caprolactone) with polymethylvinylsiloxane, poly(ethylene-co-(vinylacetate)) with dicumylperoxide, poly(D-lactide), poly(L-lactide), poly(DL-lactide) and poly(glycolide-co-($\varepsilon$-caprolactone))-segments, multiblock copolyesters from poly($\varepsilon$-caprolactone) and PEG and chain extender based on cinnamic acid groups, poly($\varepsilon$-caprolactone) dimethacrylate and n-butyl acrylate, oligo($\varepsilon$-caprolactone) diols, oligo (p-dioxanone) diols and diisocyanate, linear density polyethylene, linear low density polyethylene, high density polyethylene, and polypropylene. Catheter tube 20 is made of a, biocompatible polymeric material that has sufficient flexibility to allow for movement and advancement through the urethra of a user, but not so stiff that it would make movement and advancement of tube 20 through the urethra difficult or painful. Catheter tube 20 is made of a hydrophilic material or a material that has been made hydrophilic. Catheter tube 20 may also include a coating on at least a portion of the outer surface thereof, which when contacted by an aqueous or other liquid provides or enhances lubricity (and reduces the coefficient of friction) of catheter tube 20. Catheter tubes that are activated by agents to make the catheter tube 20 more lubricious are known and are sold in products under the trademarks VaPro™ VaPro™ Plus, distributed by Hollister Inc. of Libertyville, Ill. Additional details of such hydrophilic catheters and the activation thereof are described in U.S. Pat. No. 8,051,981, which is incorporated herein by reference. Alternatively, catheter tube 20 may be lubricated by providing a friction-reducing material such as a gel within a reservoir of introducer tip 69, discussed below, which coats catheter tube 20 as catheter tube passes through introducer tip 69. Catheter assemblies that include a gel reservoir in a protective introducer tip are sold in products under the trademarks Advance™ and Advance™ Plus, also distributed by Hollister Inc. of Libertyville, Ill. Catheter tube 20 includes a plurality of eyelet openings 21 through which urine enters the flow path of catheter tube 20.

As the catheter assemblies described herein are directed to more compact systems, such catheter tubes 20 are typically shorter in length than many intermittent catheters. Typically, a catheter tube 20 in accordance with the present disclosure has a length of approximately 100-120 mm. As shown in FIGS. 2-7, catheter tube 20 extends beyond spout 39 of drain 17 a sufficient amount such that it can be inserted into the urethra before the angle of the catheter is adjusted.

As indicated above, catheter sub-assembly 16 includes fluid junction 24 that allows for or effects relative pivotal movement of catheter tube 20 and drain 17. A catheter tube 20 that is relatively moveable to drain 17 allows for the user 78 to position and adjust catheter tube 20 and the drain 17 relative to the urine receptacle 80 (e.g., toilet), as shown in FIG. 8. This reduces the risk that the user may be unable to direct the urine into the receptacle and away from her body or clothing. An adjustable catheter tube of the type described herein also helps the user alleviate any discomfort during the withdrawal or insertion steps by allowing the user to adjust catheter tube 20 relative to the drain 17 at any angle that is most comfortable for the user. Typically, but without limitation, catheter tube 20 and drain 17 may be adjusted to a variety of different angles anywhere between 0° and approximately 120° and more typically between approximately 45° and approximately 90°. However, as shown in other embodiments below, angles greater than 90° are also possible.

Fluid junction 24 carries catheter tube 20 or is otherwise attached to it. In turn, fluid junction 24 and tube 20 are carried by handle 18 or drain 17. In one embodiment, fluid junction 24 may be a rotary member that rotates about an axis to allow for the relative pivotal or hinged movement of tube 20 and handle 18. In one embodiment, rotary member may be a spherical member as shown in FIGS. 4-7 or a spool, as shown in FIGS. 9-13. In addition, fluid junction 24 may also serve to establish flow communication between the flow path of catheter tube 20 and the flow path provided by drain 17. Fluid junction 24 is disposed at distal end of catheter sub-assembly 16 and may be received in the socket 25 defined by handle 18 (and optionally cap 26 as shown in FIGS. 4-7). Fluid junction 24 may be integrally molded with catheter tube 20, or separately molded and attached thereafter.

Fluid junction 24 includes an internal flow path that establishes communication between the flow path of catheter tube 20 and the flow path defined by drain 17. As shown in FIGS. 4, 6 and 7, preferably flow path 44 in fluid junction 24 is non-linear, thereby allowing for flow to commence when catheter tube 20 is adjusted to an angle $\alpha$ defined by catheter tube 20 and drain 17 (FIG. 4) of less than approximately 180°. In a preferred embodiment, angle $\alpha$ may be between approximately 60° and approximately 120°. More preferably, angle $\alpha$ may be between approximately 80° and approximately 110° and even more preferably, approximately 90°. Providing a flow path 44 that is non-linear allows catheter tube 20 to be placed in a variety of positions that establish flow and provide a comfort level that is determined by the user.

Movement of catheter tube 20 from a non-deployed position to a deployed position (and vice versa) may be accomplished by manual movement of catheter tube 20. In an alternative embodiment, movement to deploy catheter tube 20 to its desired orientation or to establish flow may be accomplished by an actuator connected to fluid junction 24. FIGS. 9A-9B show one such alternative, whereby fluid junction 24 is provided as a different type of rotary member, such as a spool. Fluid junction 24 includes a flow path extending therethrough. Flow path 44 of the fluid junction 24 of the embodiment shown in FIGS. 9A and 9B may likewise be non-linear, whereby movement of catheter tube 20 establishes flow between urine flowing through the flow path of catheter tube 20 and the spout portion of handle 18. In the embodiment of catheter sub-assembly 116 shown in FIGS. 9A-9B, movement of catheter tube 20 is accomplished by knob 46, which is connected to fluid junction 24 through handle 18. Turning knob 46 pivotally moves catheter tube 20. In the embodiment of FIGS. 9A-9B, catheter tube 20 includes hub 49 at the distal end of tube 20 and is joined to fluid junction 24 at port 48 by hub 49. An outlet port in fluid junction 24 is then aligned with drain 17 terminating in spout 39 of handle 18. While the embodiment of FIGS. 9A and 9B show an open drain 17, it will be appreciated that handle 18 may also include a dividing wall 19, as shown in FIGS. 2-7, which bifurcates handle 18 into a first portion which supports catheter tube 20 and an internal lumen 38, as previously described.

In a further alternative shown in FIGS. 10A-10B, catheter tube 20 of catheter sub-assembly 216 may be attached to port 48 at hub 39 that surrounds catheter tube 20 at the distal end of catheter assembly 216. In the embodiments of FIGS. 10A-10B, catheter sub-assembly 216 includes a laterally spaced and offset (from catheter tube 20) drain shown as drainage tube 56. Drainage tube 56 extends from and communicates with fluid junction 24, as shown. Drainage tube 56 is relatively rotatable with respect to catheter tube 20 and, as shown in FIGS. 10A-10B, can be pivoted to form an angle with catheter tube 20 that is greater than 90° and up to 180°. Fluid junction 24 includes an internal flow path 54 that communicates with the internal flow path of catheter tube 20 through port 48. Furthermore, as shown in earlier FIGS. 9A-9B, catheter sub-assembly 216 of FIGS. 10A-10B may likewise include a flow controller 50 that controls flow through catheter assembly 216. In one embodiment, shown in FIGS. 10C-10D, flow controller 50 may be an on/off switch or button, which when pressed either blocks or opens flow through flow path 54 of drainage tube 56. For example, FIG. 10C shows flow controller 50 in the "open flow" position whereby urine drained from the urinary canal of the subject flows through the flow path of catheter tube 20, enters fluid junction 24 and exits through drainage tube 56. Apertures 50b and 50c in flow controller 50 are aligned with the flow paths of catheter tube 20 and drainage tube 56 in the "open flow" position. FIG. 10D shows flow controller 50 in the "closed flow" position. By pushing actuator 50a, apertures 50b and 50c in flow controller 50 are moved out of alignment with flow paths of catheter tube 20 and drainage tube 56, thereby blocking flow.

Figure 11B:
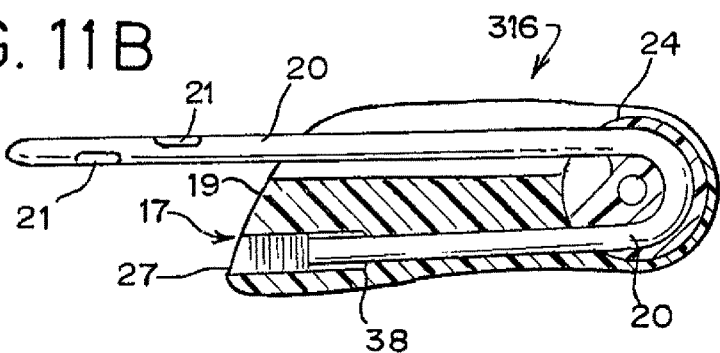
FIG. 11B is a cross-sectional side view of the catheter assembly of FIG. 11A with the catheter tube in its initial position.
Figure 11C:
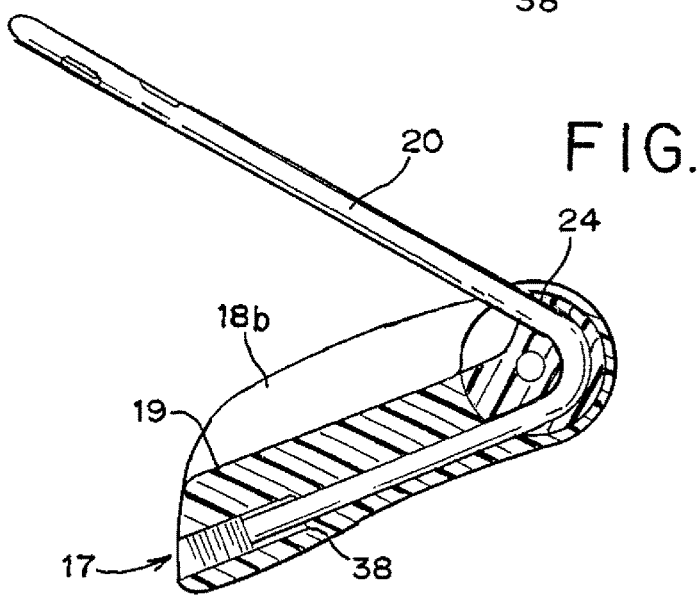
FIG. 11C is a cross-sectional side view of the catheter assembly of FIG. 11A with the catheter tube in a deployed position.
Figure 12A:
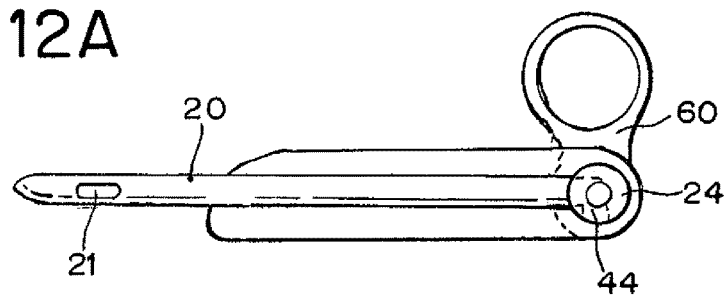
FIG. 12A is a is a perspective view of a further embodiment of a catheter sub-assembly of the present disclosure.
Figure 12B:
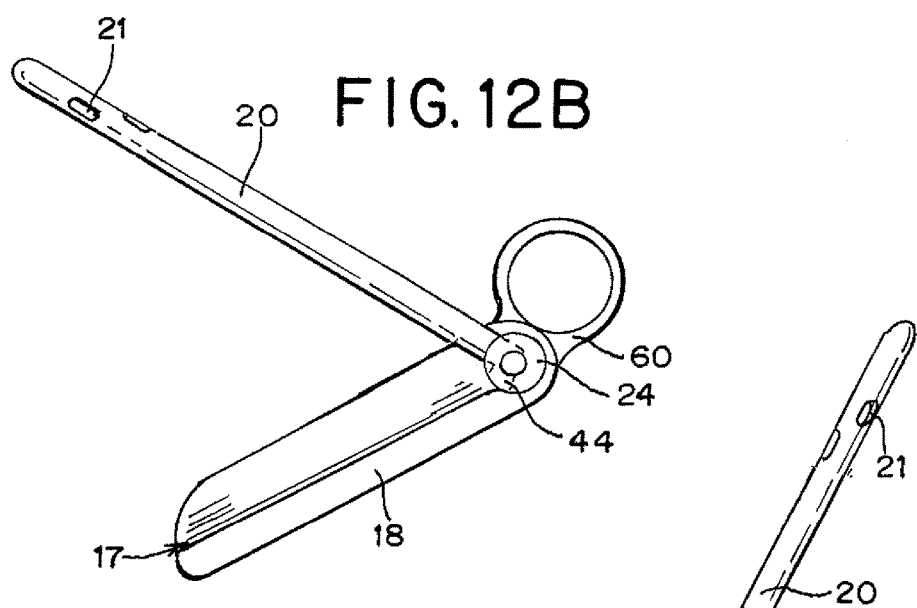
FIG. 12B is a cross-sectional side view of the catheter assembly of FIG. 12A with the catheter tube in its initial position.
Figure 12C:
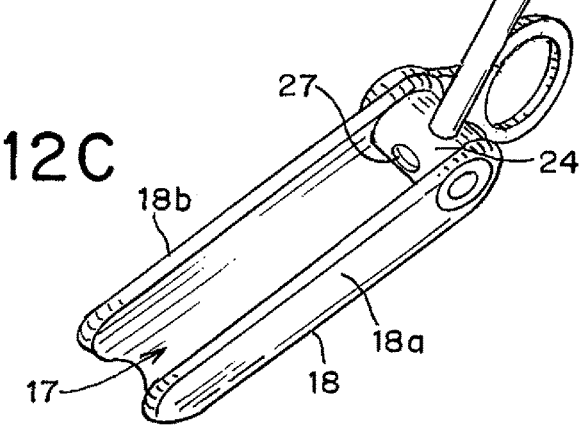
FIG. 12C is a cross-sectional side view of the catheter assembly of FIG. 12A with the catheter tube in a deployed position.

A further alternative of the catheter sub-assembly disclosed herein is shown in FIGS. 11A-11C. In the catheter sub-assembly 316 of FIGS. 11A-11C, fluid junction 24 may be a rotary member provided as, for example, a spool wherein catheter tube 20 extends through the fluid junction 24 and handle 18 and communicates with an outlet port 27. As shown in FIGS. 11A-11C, catheter tube 20 extends longitudinally and is curved as it extends through fluid junction 24, communicating with an outlet port 27 in handle 18, as shown in FIG. 11C. The embodiment of FIGS. 11A-11C include an internal lumen 38 of the type disclosed in connection with FIGS. 4-7 with a dividing wall 19, upon which catheter tube 20 rests when in its non-deployed orientation. As shown in the FIGS. 4-7, catheter tube 20 may be manually adjusted by the user to provide the desired orientation of the tube. Alternatively, catheter tube 20 may be adjusted or rotated by providing an actuator of the type previously described in connection with FIG. 9A-9B, 10A-10B, or as shown in FIGS. 12A and 12B. As shown in FIGS. 12A-12B, actuator is provided as a ring 60, which is connected to fluid junction 24. Ring 60 may be particularly useful for users of the catheter assemblies disclosed herein who have diminished dexterity.

Figure 13A:
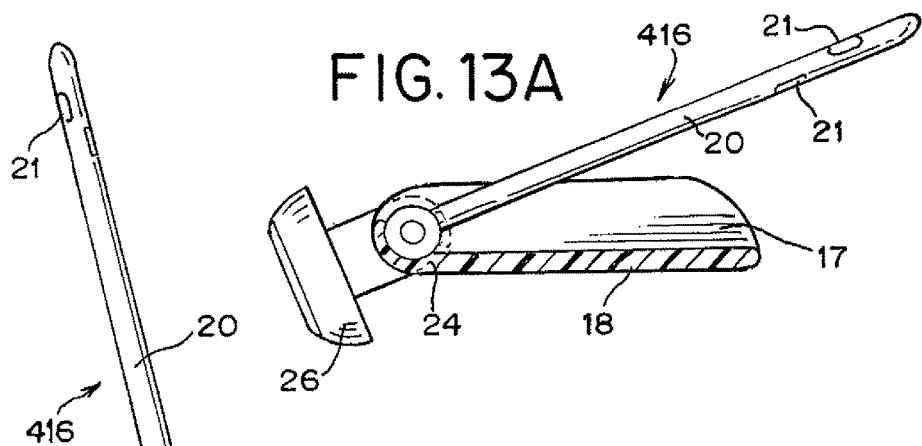
FIG. 13A is a cross-sectional side view of another embodiment of a catheter assembly of the present disclosure with the catheter tube and handle in a first relatively pivoted position.
Figure 13B:
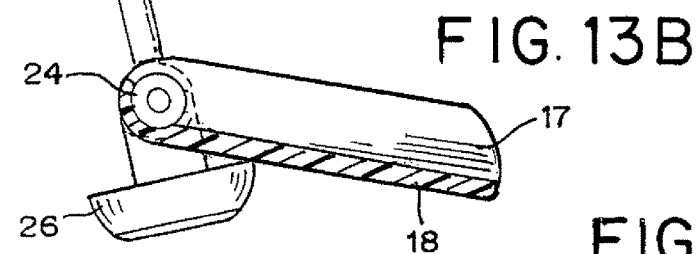
FIG. 13B is a cross-sectional side view of the catheter sub-assembly of FIG. 13A with the catheter tube and handle in a second relatively pivoted position.
Figure 13C:
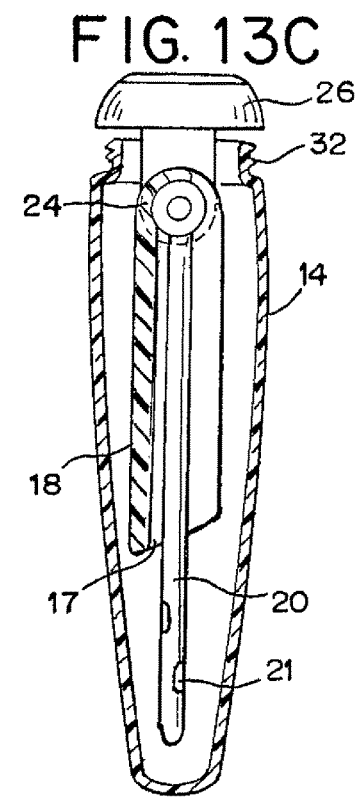
FIG. 13C is a cross-sectional side view of the catheter sub-assembly of FIGS. 13A-13B housed within a package or receiver.
Figure 14:
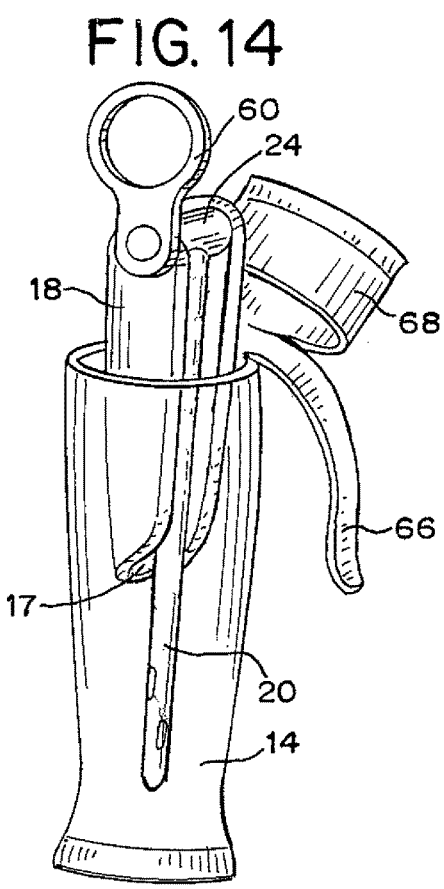
FIG. 14 shows an alternative package for housing a catheter sub-assembly of the present disclosure.
Figure 15:
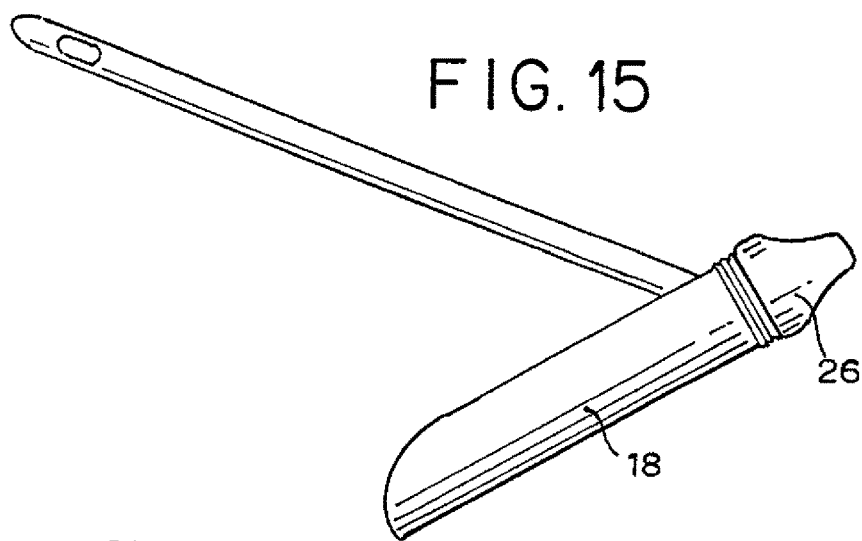
FIG. 15 is a side view of the catheter sub-assembly of the present disclosure without a sleeve over the catheter tube.
Figure 16:
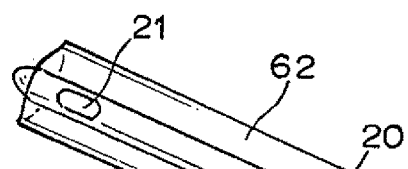
FIG. 16 is a side view of the catheter sub-assembly of the present disclosure with a full-length sleeve over the catheter tube.
Figure 17:
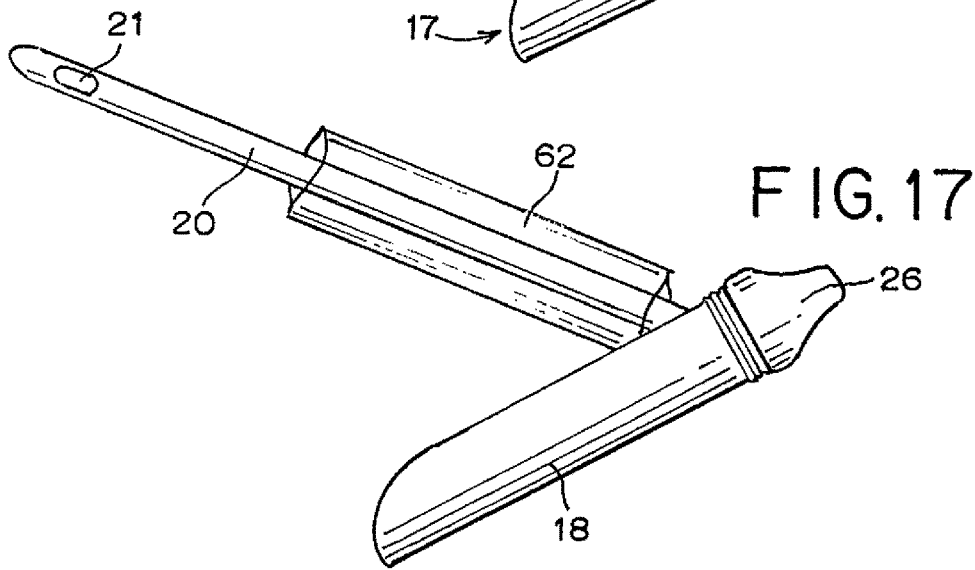
FIG. 17 is a side view of the catheter sub-assembly of the present disclosure with a partial sleeve over the catheter tube.

FIGS. 13 and 14 show an additional embodiment of the catheter assembly disclosed herein. FIGS. 13A-13B show a catheter sub-assembly 416 where cap 26 is relatively rotatable with handle 18 defining drain 17. Catheter sub-assembly 16 of FIGS. 13A-13B includes a fluid junction 24 wherein cap 26 and catheter tube 20 are aligned and relatively rotatable with handle 18. As in the embodiments described above, fluid junction 24 may include an outlet through which urine exits and flows down to spout 39. FIG. 13C shows a catheter assembly of the type shown in FIGS. 13A and 13B with a receiver 14 for use therewith. Receiver 14 includes an engagement surface such as (external) threaded surface 32 for engagement by corresponding threads on cap 26.

FIG. 14 shows a further packaging alternative where catheter sub-assembly 416 (or 16, 116, 216, 316) does not include and integral cap 26. In the embodiment of FIG. 14, receiver 14 may be a soft, flexible package that includes a tear-away tab 66 that separates cap portion 68 from the remainder of the flexible receiver 14. Materials suitable for use in the receiver as shown in FIG. 14 include polyethylene, polypropylene, and the like.

As shown in FIGS. 15-18, catheter assemblies of the type described herein and shown in all of the Figures may also be provided with a partial or full-length sleeve over catheter tube 20. Sleeve 62 allows the user to manually handle catheter tube 20 without directly contacting the tube itself. Such "no touch" sleeves are typically made of a thin polymeric material that can be easily folded or bunched by the user as the catheter tube 20 is advanced into the urethra. Sleeve 62 may be formed of any variety of thin, flexible polymeric materials, such as polyethylene, plasticized PVC, polypropylene, polyurethane, or elastomeric hydrogels. In addition, as shown in FIG. 18, catheter sub-assembly 16 may also include an introducer tip 69 located at the proximal tip end of catheter tube 20. Introducer tip 69 protects the proximal end tip of catheter tube 20 during insertion into the urethra from bacteria residing in the distal urethra and includes a plurality of slits in its proximal tip to allow for deployment of catheter tube 26, as shown in FIG. 18.

Finally, FIG. 20 shows a catheter assembly 10 of the type disclosed herein. In the embodiment of FIG. 20, receiver may be provided with a hydration element 70 placed within interior chamber of receiver 14. As discussed above, catheter tubes made in accordance with the present disclosure are typically made of a hydrophilic material that includes a coating on the outer surface thereof. The coating may be activated by an aqueous or non-aqueous solution in order to make the outer surface of catheter tube 20 more lubricious.

Hydration element 70 provides a source of fluid suitable for activating the outer coating on the hydrophilic material of catheter tube 20. The fluid may be provided to catheter tube 20 as a liquid or, more preferably, a vapor. The hydrating element 70 may provide water or other aqueous solution as a vapor fluid. Hydration element 70 is preferably contained within the interior chamber of receiver 14, as shown in FIG. 20.

In one embodiment, hydration element 70 is provided as a sealed sachet or pillow 72 that includes water or other fluid within it. Hydration element 70 is preferably made of a suitable material that is selected to release the hydrating agent through its walls. In addition or alternatively, hydration element 70 may include an insert made of a material that retains water or other aqueous fluid. In one embodiment, the hydration element 70, with or without the insert, may be made of a polymeric material that is vapor permeable but liquid impermeable. Hydration element 70 may be freely placed within the interior chamber of receiver 14. Alternatively, hydration element 70 or a portion thereof may be secured to the inner wall of receiver 14.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A catheter sub-assembly comprising a handle including lateral walls and defining a fluid drain, a fluid junction including a flow path defined therein, a catheter tube defining a flow path therein and communicating with and carried by said junction, said catheter tube and said fluid drain being relatively pivotally movable about said junction, wherein said handle is configured to receive said catheter tube in a non-deployed position between said lateral walls.

2. The catheter sub-assembly of claim 1 wherein said drain defines a flow path.

3. The catheter sub-assembly of claim 2 wherein said drain flow path is defined by an enclosed lumen within said handle.

4. The catheter sub-assembly of claim 1 wherein said handle comprises a terminal proximal end said catheter tube comprises a distal portion and a proximal portion, wherein said proximal portion of said catheter tube includes at least a pair of eyelet openings and extends beyond said proximal end of said handle when said catheter tube is in its initial state.

5. The catheter sub-assembly of claim 4 wherein said fluid junction comprises a rotary member.

6. The catheter assembly of claim 5 wherein said rotary member is selected from one of a generally spherical member or a spool.

7. The catheter sub-assembly of claim 1 wherein said flow path through said fluid junction is non-linear.

8. The catheter sub-assembly of claim 1 further comprising a flow controller associated with said fluid junction.

9. The catheter assembly of claim 8 further comprising a socket in said handle for receiving said fluid junction.

10. The catheter sub-assembly of claim 9 wherein said fluid junction and said catheter tube comprises an integrally molded unit.

11. The catheter sub-assembly of claim 1 further comprising an actuator for effecting relative pivotal movement of said catheter tube and said handle.

12. The catheter sub-assembly of claim 1 further comprising a sleeve over at least a portion of said catheter tube.

13. The catheter sub-assembly of claim 1 further comprising an introducer tip at the proximal tip of said catheter tube.

14. The catheter sub-assembly of claim 1 further comprising an engagement surface for allowing attachment of one or both of a cap and a receiver.

15. The catheter sub-assembly of claim 14 wherein said engagement surface comprises a threaded surface.

16. The catheter sub-assembly of claim 14 further comprising a receiver cap.

17. The catheter sub-assembly of claim 16 wherein said receiver cap has a plurality of depressions.

18. The catheter sub-assembly of claim 1, said catheter assembly having a central longitudinal axis wherein said catheter tube is adjustable to an angle no greater than 90° from said central longitudinal axis.

19. The catheter sub-assembly of claim 1 further comprising a port adapted for attachment of a collection container.

20. A catheter sub-assembly comprising a drainage tube, a fluid junction including a flow path defined therein, a catheter tube defining a flow path therein and communicating with and carried by said junction, and a flow controller for opening and blocking flow through said drainage tube, said catheter tube and said drainage tube being relatively pivotally movable about said junction, wherein said drainage tube is laterally spaced from said catheter tube.

21. The catheter assembly of claim 20 further comprising an actuator for allowing and blocking flow.

22. The catheter assembly of claim 14 wherein said catheter assembly is configured to be carried within a receiver.

* * * * *